(12) United States Patent
Nedwed et al.

(10) Patent No.: US 10,152,519 B2
(45) Date of Patent: Dec. 11, 2018

(54) OPTIMIZED SPECTRAL MATCHING AND DISPLAY

(71) Applicant: Bio-Rad Laboratories, Inc., Hercules, CA (US)

(72) Inventors: Karl Nedwed, Graz (AT); Ty Abshear, Grand Junction, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 310 days.

(21) Appl. No.: 15/060,260

(22) Filed: Mar. 3, 2016

(65) Prior Publication Data

US 2016/0259792 A1 Sep. 8, 2016

Related U.S. Application Data

(60) Provisional application No. 62/128,813, filed on Mar. 5, 2015.

(51) Int. Cl.
*G06F 17/30* (2006.01)
*G06K 9/52* (2006.01)
(Continued)

(52) U.S. Cl.
CPC ......... *G06F 17/3053* (2013.01); *G01N 21/35* (2013.01); *G06F 17/30554* (2013.01);
(Continued)

(58) Field of Classification Search
CPC combination set(s) only.
See application file for complete search history.

(56) References Cited

U.S. PATENT DOCUMENTS 6,816,605 B2 * 11/2004 Rowe ................. A61B 5/0059
                                                     382/115
7,698,098 B2 *  4/2010 Ritter ..................... G01N 21/35
                                                     250/282

(Continued)

FOREIGN PATENT DOCUMENTS

EP    2 284 518 A1    2/2011
JP    H04 364490 A   12/1992

OTHER PUBLICATIONS

International Search Report and Written Opinion from Appl. No. PCT/US2016/020715, dated May 27, 2016.

(Continued)

*Primary Examiner* — Farhan M Syed
(74) *Attorney, Agent, or Firm* — Kilpatrick, Townsend & Stockton LLP

(57) ABSTRACT

Systems, methods, and apparatuses are provided for identifying an optimal spectral match and potentially display the compared spectra. A sample spectrum of a sample substance can be compared to reference spectra to identify matches, thereby determining possibilities for what the sample substance is. Correction parameter(s) may be used for the sample spectrum and/or the reference spectrum. Initial value(s) for the correction parameter(s) can be applied to the sample spectrum and/or a reference spectrum, and a similarity score can be determined. The value(s) for the correction parameter(s) can be updated and iteratively improved to provide an optimal similarity score that satisfies a convergence criterion. Data about the reference substances having optimal similarity scores that are above a threshold can be output to a user, e.g., the reference spectra can overlay the sample spectrum. A user can then make a final determination of which reference substance corresponds to the sample substance.

20 Claims, 8 Drawing Sheets

(51) Int. Cl.
  *G06K 9/62* (2006.01)
  *G06T 11/20* (2006.01)
  *G01N 21/35* (2014.01)
  *G06K 9/46* (2006.01)
  *G01N 21/552* (2014.01)

(52) U.S. Cl.
  CPC ............. *G06K 9/4661* (2013.01); *G06K 9/52* (2013.01); *G06K 9/6215* (2013.01); *G06K 9/6218* (2013.01); *G06T 11/203* (2013.01); *G01N 21/552* (2013.01); *G01N 2201/121* (2013.01); *G01N 2201/127* (2013.01); *G01N 2201/129* (2013.01); *G06K 2209/05* (2013.01)

(56) References Cited

U.S. PATENT DOCUMENTS

| | | | | |
|---|---|---|---|---|
| 7,973,936 | B2* | 7/2011 | Dantus | G01J 11/00 356/451 |
| 9,417,257 | B2* | 8/2016 | Butters | G01N 37/005 |
| 9,688,743 | B2* | 6/2017 | Schmidt | A61K 49/0021 |
| 2003/0223621 | A1* | 12/2003 | Rowe | A61B 5/0059 382/115 |
| 2006/0187974 | A1* | 8/2006 | Dantus | G01J 11/00 372/9 |
| 2007/0061091 | A1 | 3/2007 | Schweitzer et al. | |
| 2009/0210194 | A1* | 8/2009 | Ritter | G01N 21/35 702/179 |
| 2012/0309636 | A1* | 12/2012 | Gibbons | B01L 3/0275 506/9 |
| 2013/0096883 | A1* | 4/2013 | Bradley | G01N 21/35 702/189 |
| 2014/0350392 | A1 | 11/2014 | Lundqvist et al. | |
| 2015/0185234 | A1* | 7/2015 | Gibbons | B01L 3/0275 506/9 |
| 2015/0199010 | A1* | 7/2015 | Coleman | A61B 5/0006 345/156 |
| 2016/0006928 | A1* | 1/2016 | Gibbons | B01L 3/0275 348/79 |

OTHER PUBLICATIONS

Author Unknown, "Advanced ATR Correction to Convert ATR Spectra to Transmission Spectra," Shimadzu Application News, No. A476, 2 pages (Feb. 2014).

Author Unknown, "Standard Guide for Use of Spectral Searching by Curve Matching Algorithms with Data Recorded Using Mid-Infrared Spectroscopy," ASTM International, Designation E2310-04, 10 pages (Mar. 2009).

Lan et al., "Automatic baseline correction of infrared spectra," *Chinese Optics Letters*, 5(10):613-616 (Oct. 2007).

Nunn et al., "Advanced ATR Correction Algorithm," Thermo Scientific, Application Note 50581, 4 pages (2008).

Yu et al., "A New Approach for Spectra Baseline Correction Using Sparse Representation," 10$^{th}$ IASTED International Conference on Signal Processing, Pattern Recognition and Applications (SPPRA), Feb. 12-14, 2013, Innsbruck, Austria (7 pages).

Extended European Search Report for EP Application No. 16759503.2 dated Jul. 25, 2018.

Frewen et al. "Analysis of Peptide MS/MS Spectra from Large-Scale Proteomics Experiments Using Spectrum Libraries," Anal. Chem., vol. 78., No. 16, Aug. 2006.

Stein et al. "Optimization and Testing of Mass Spectral Library Search Algorithms for Compound Identification," Journal of the American Society for Mass Spectrometry, Elsevier Science Inc., vol. 78, No. 16, pp. 859-866, May 1994.

* cited by examiner

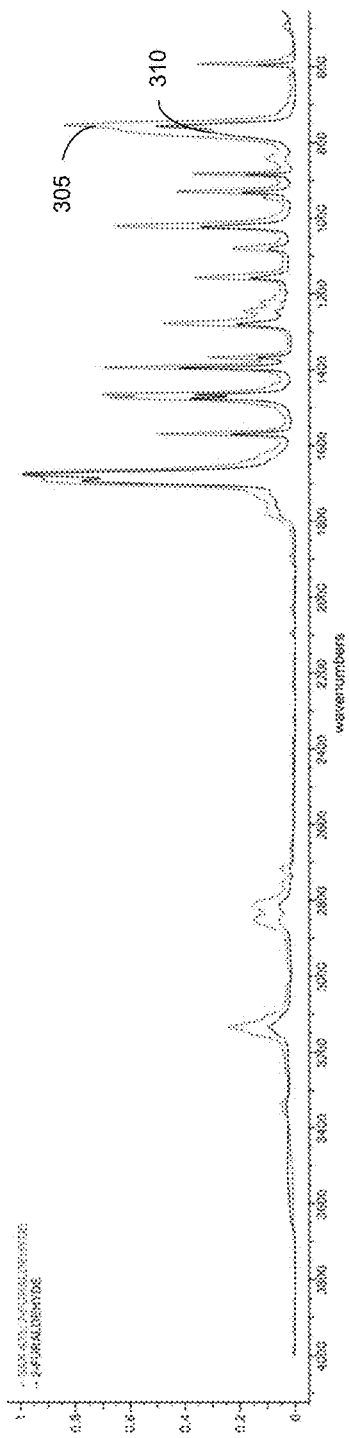
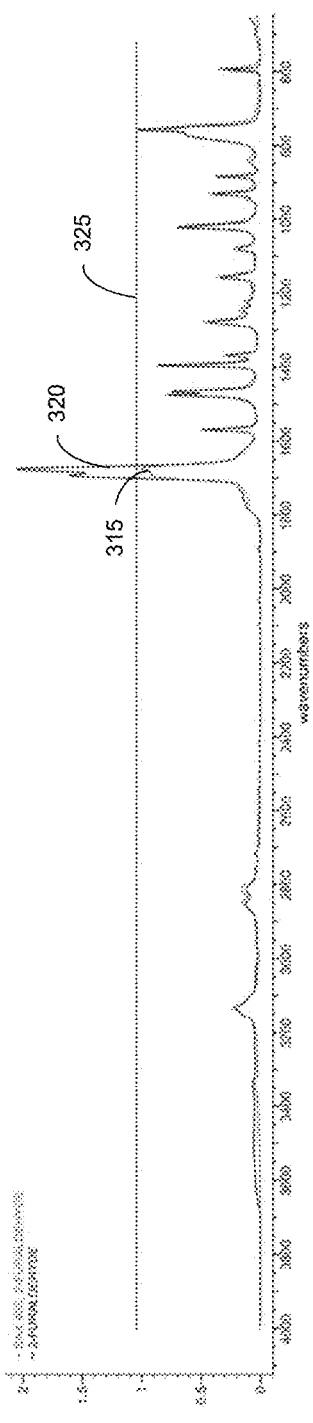
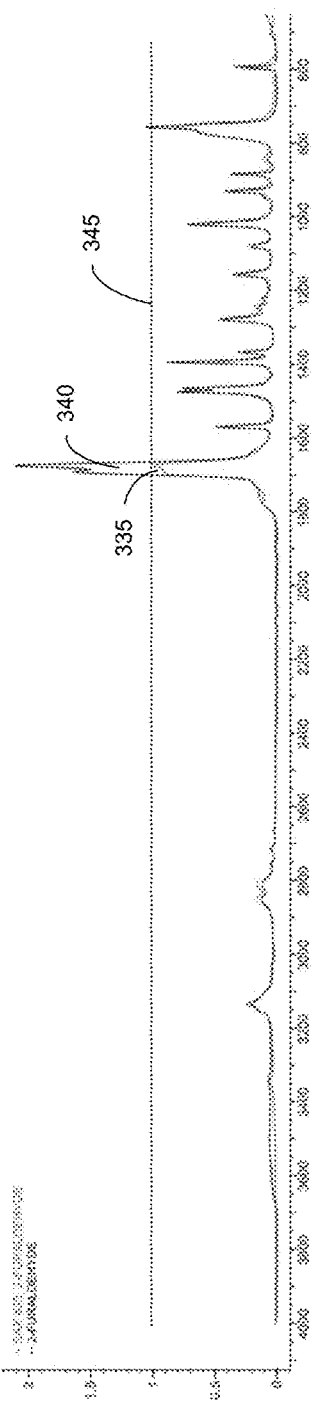

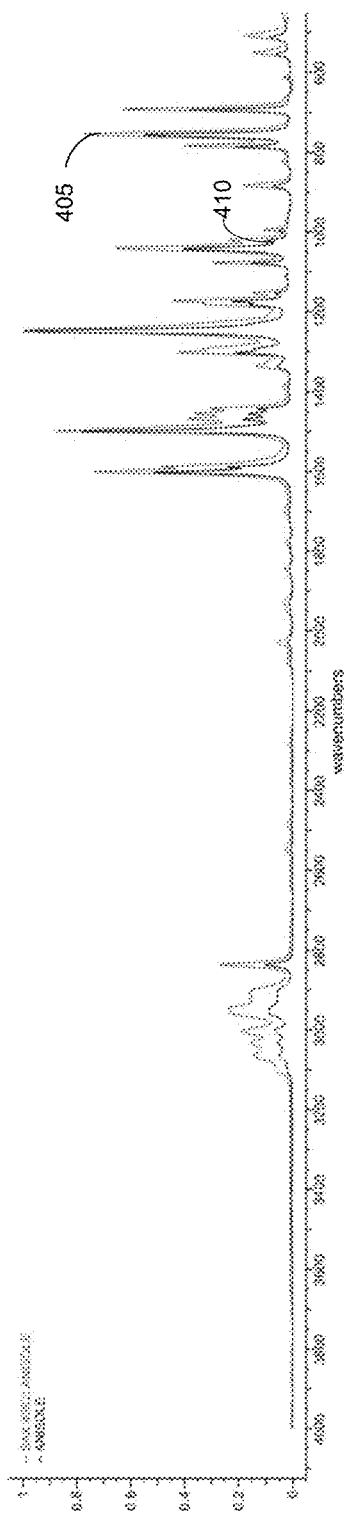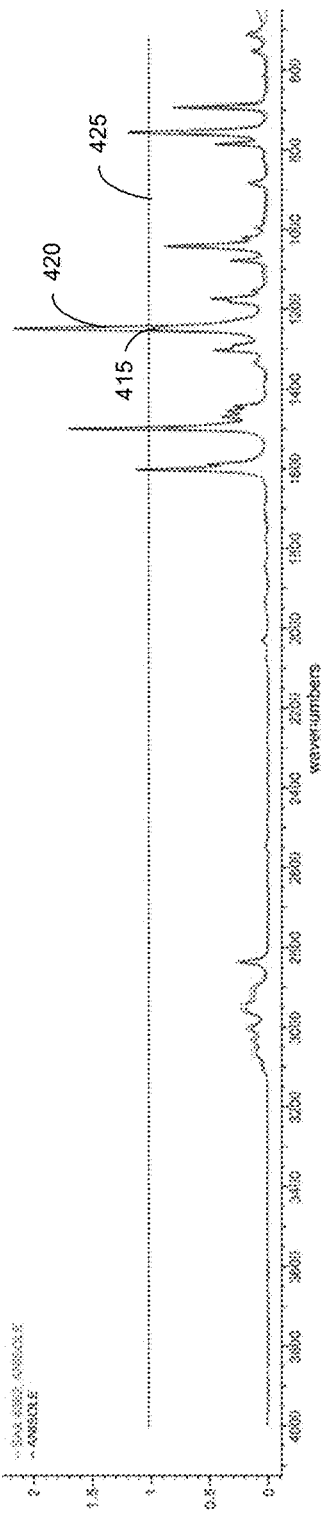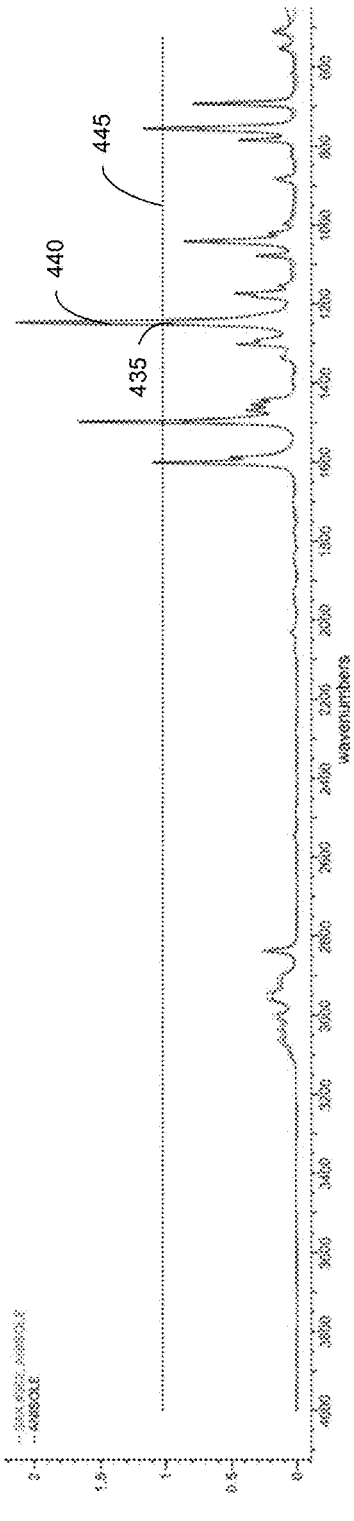

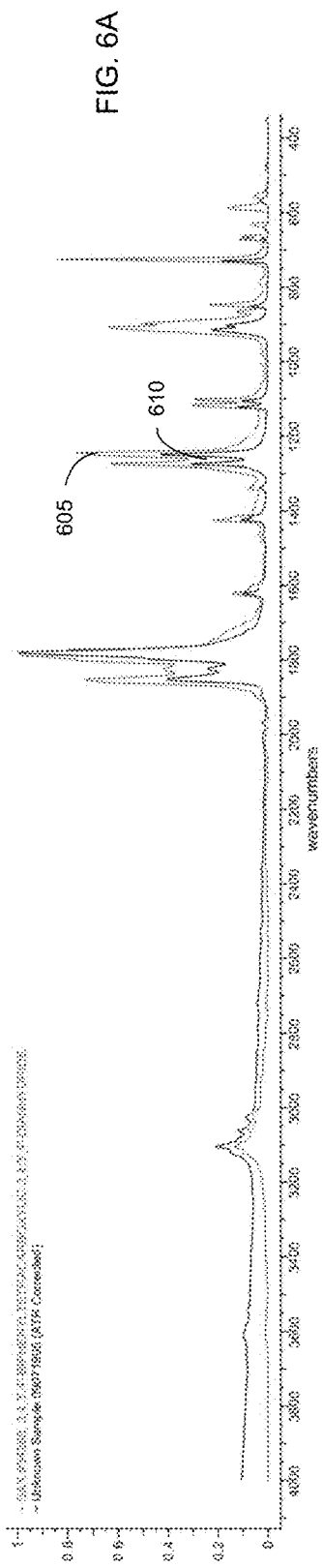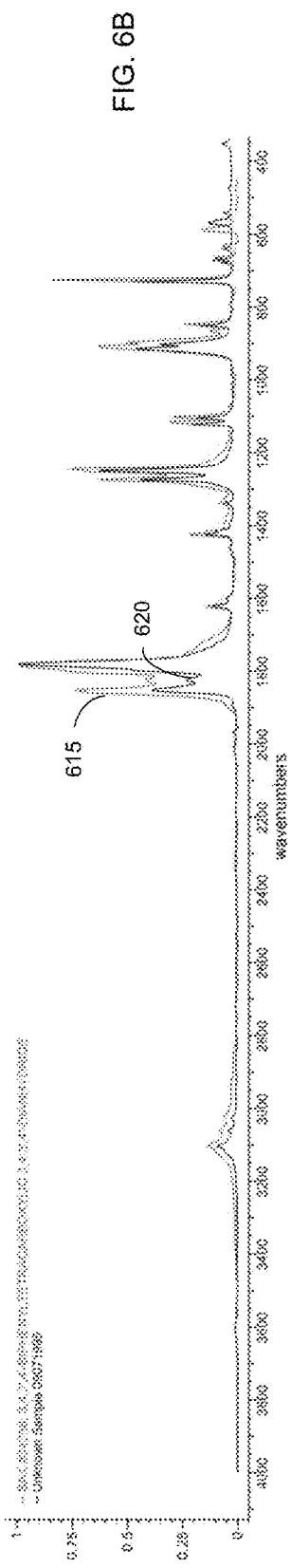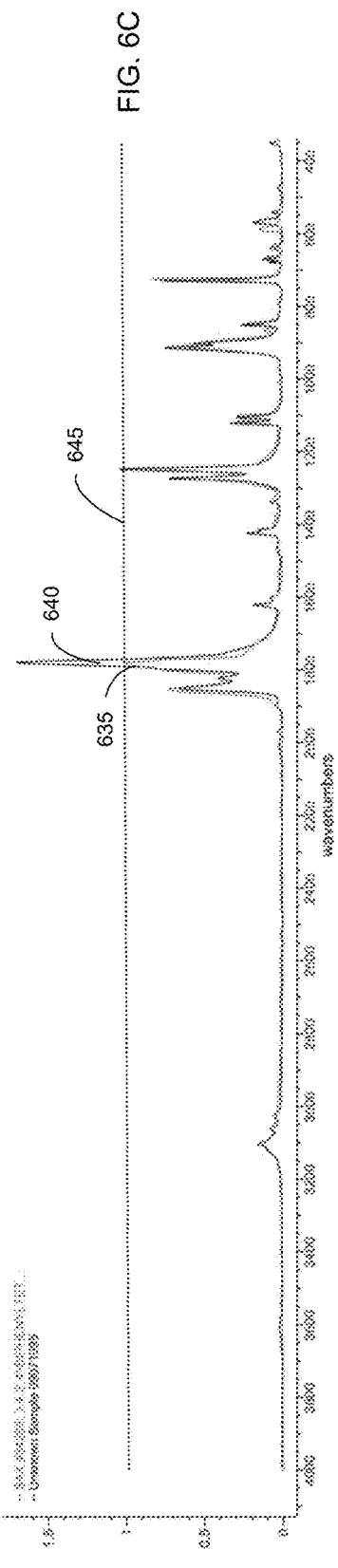

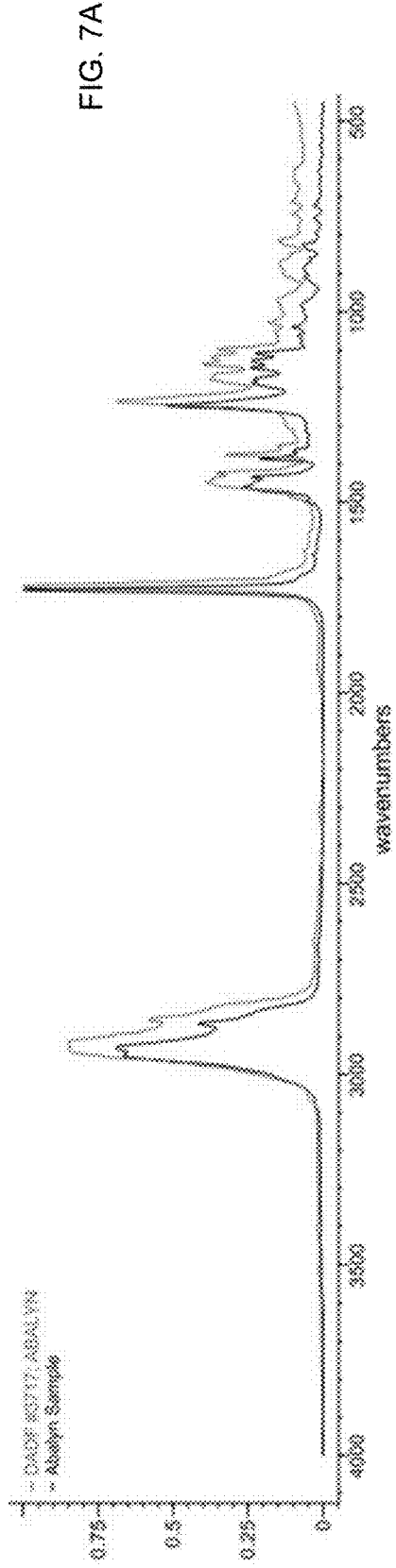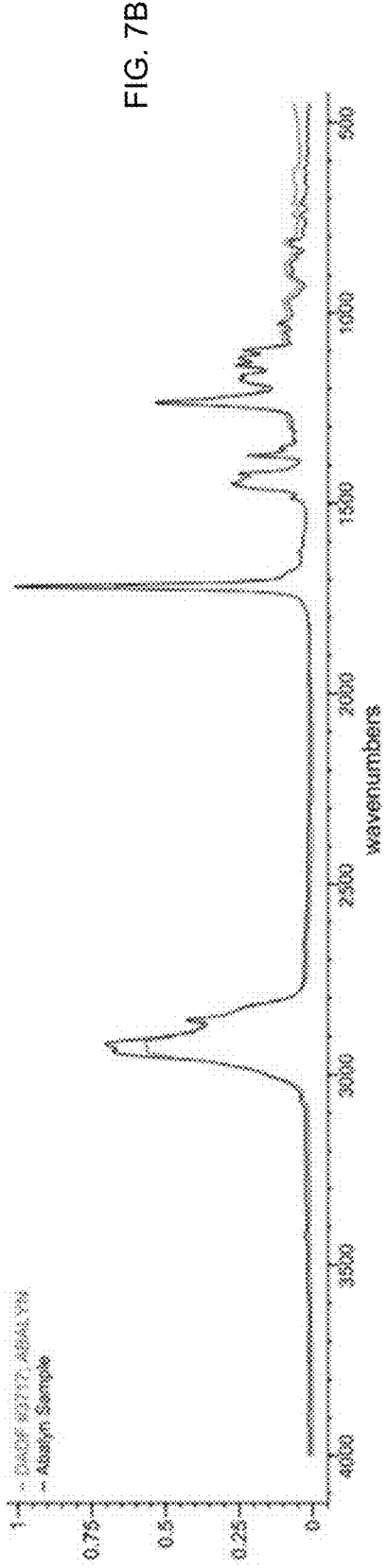

OPTIMIZED SPECTRAL MATCHING AND DISPLAY

CROSS-REFERENCES TO RELATED APPLICATIONS

The present application claims priority from and is a non-provisional application of U.S. Provisional Application No. 62/128,813, entitled "Optimized Spectral Matching And Display," filed Mar. 5, 2015, the entire contents of which are herein incorporated by reference for all purposes.

FIELD

This disclosure relates to spectrographic analysis, and more particularly to analyzing spectra to determine a matching substance.

BACKGROUND

A scientist often wants to determine substances that are within a sample. One way to determine a substance is to perform spectroscopy on the substance to obtain a sample spectrum. Then, one can analyze the sample spectrum to identify aspects of the spectrum that correspond to a particular substance. As part of this analysis, one can compare the sample spectrum to a reference spectrum of a known substance.

A problem is that there are many reference spectra, which may be somewhat similar to each other. Techniques can use a computerized analysis to quantify similarities between a sample spectrum and a reference spectrum to facilitate the comparison. However, a sample spectrum of a substance may not always exactly mirror a reference spectrum of the same substance. For example, there can be shifts in a baseline, or the two spectra may be obtained using different techniques. Thus, the differences in the two spectra are not because they are of different substances, but can be due to experimental conditions for how the spectra were obtained.

To address these issues, one typically performs some sort of correction on the sample spectrum. However, the current corrections performed often are not sufficient to identify the correct substance.

Embodiments described herein can address these and other problems.

BRIEF SUMMARY

Embodiments can provide systems, methods, and apparatuses for identifying an optimal spectral match and potentially display the compared spectra, e.g., in a more intelligent, understandable visualization. A sample spectrum of a sample substance can be compared to a plurality of reference spectra to identify matches, thereby determining possibilities for what at least a portion of the sample substance is. Correction parameter(s) may be used for the sample spectrum and/or the reference spectrum. Initial value(s) for the correction parameter(s) can be applied to the sample spectrum and/or a reference spectrum, and a similarity score can be determined. The value(s) for the correction parameter(s) can be updated and iteratively improved to provide an optimal similarity score that satisfies one or more convergence criteria. Data about the reference substances having optimal similarity scores that are above a threshold can be output to a user, e.g., the reference spectra can overlay the sample spectrum. A user can then make a final determination of which reference substance corresponds to the sample sub stance.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 3A shows an original result of 2-Furaldehyde with match score of 87.6%. FIG. 3B shows an iteratively optimized clipping correction and display result of 2-Furaldehyde with match score of 96.2% according to embodiments of the present invention. FIG. 3C shows iteratively optimized corrections and display result of 2-Furaldehyde with match score of 97.6% according to embodiments of the present invention.

FIG. 4A shows an original result of Anisole with match score of 87.8%. FIG. 4B shows an iteratively optimized clipping correction and display result of Anisole with match score of 95.4% according to embodiments of the present invention. FIG. 4C shows iteratively optimized corrections and display result of Anisole with match score of 97.6% according to embodiments of the present invention.

FIG. 6A shows an original result of 3,4,3',4'-Biphenyltetracarboxylic 3,4:3',4'-dianhydride with HQV of 57.9%. FIG. 6B shows a baseline correction result of 3,4,3',4'-Biphenyltetracarboxylic 3,4:3',4'-dianhydride with HQV of 83.7% according to embodiments of the present invention. FIG. 6C shows an iteratively optimized correction and display result of 3,4,3',4'-Biphenyltetracarboxylic 3,4:3',4'-dianhydride with HQV of 89.4% according to embodiments of the present invention.

FIG. 7A shows an original result for an Abalyn Sample with HQV of 79.3% according to embodiments of the present invention. FIG. 7B shows an iteratively optimized result for an Abalyn Sample with HQV of 98.3% according to embodiments of the present invention.

TERMS

Figure 1:
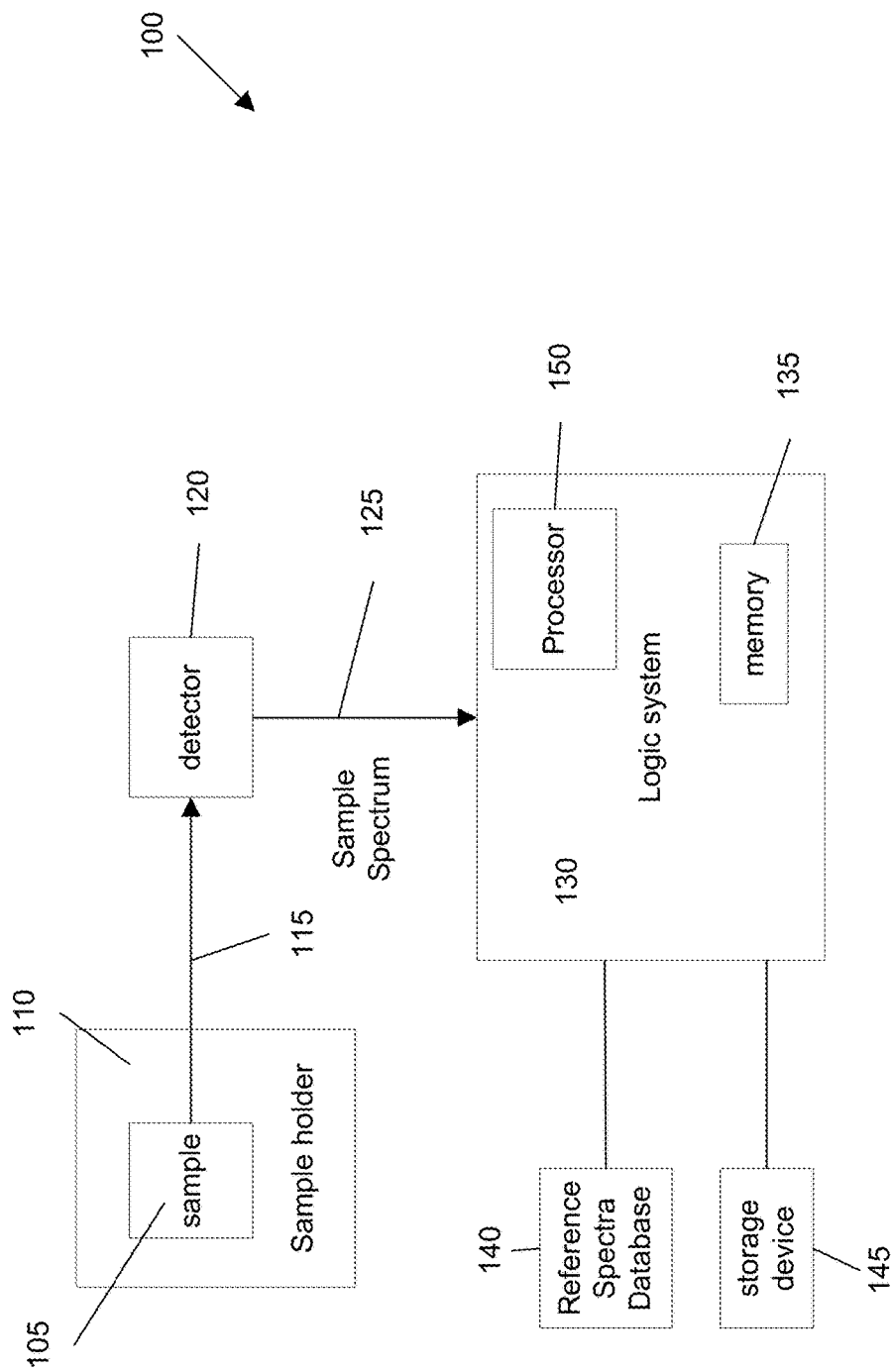
FIG. 1 illustrates a system 100 for obtaining spectra and determining matching spectra according to embodiments of the present invention.

A "spectrum" of a sample corresponds to a set of data points, where each data point includes at least two values. A first value corresponds to a discriminating property of the spectrum, such as a mass or frequency. The property is discriminating in that the particles are differentiated in the spectrum based on values for the property. The second value corresponds to an amount of particles measured from the sample that have the first value for the property. For instance, a data point can provide an amount of ions having a particular mass-to-charge ratio (also sometimes referred to as "mass").

A "similarity score" or hit quality value (HQV) refers to a numeric value that demonstrates how similar two spectra are.

The term "optimal" refers to any value that is determined to be numerically better than one or more other values. For example, an optimal value is not necessarily the best possible value, but may simply satisfy a criterion (e.g. a change in a cost function from a previous value is within tolerance). Thus, the optimal solution can be one that is not the very best possible solution, but simply one that is better than another solution according to a criterion. Such an optimal solution encompasses 'near-optimal' solutions.

DETAILED DESCRIPTION

Systems, apparatuses, and methods are provided that allow a sample spectrum (e.g., defined as a series of X-Y data points) to be compared to another spectrum in an iterative process. The iterative process can apply one or more corrections to the X-Y data points of one spectrum or to the other spectrum. One or more parameters in the correction can be adjusted in each iteration to find the parameter(s) that give the best match between the spectra, e.g., as defined by a scoring algorithm that can assign a relative numerical value to the match of the two spectra for a given iteration. Thus, the values of the one or more parameters can be iteratively optimized.

Once the parameter(s) for the correction(s), which give the best matching of one spectrum to the other corrected spectrum as defined by the scoring algorithm, have been determined, the correction(s) using the parameter(s) that give the best match can be applied to the appropriate spectrum. Both spectra can be corrected with respective parameters. The spectra with correction(s) can be displayed visually, e.g., by plotting the curves graphically in an overlapping, stacked, or offset fashion.

In spectroscopy applications, embodiments can allow users to identify optimal spectral matches within reference databases and visualize the comparative results in a way that is more discernible to the human eye. Various types of spectroscopy can be used. Example spectroscopic techniques include Infrared (Near-IR, Mid-IR, Far-IR), Raman, Mass Spectrometry (MS), Chromatography, Nuclear Magnetic Resonance (NMR), Electron Spin Resonance (ESR), X-Ray Diffraction (XRD), X-Ray Fluorescence (XRF), Fluorescence, Ultraviolet-Visible (UV-Vis), and Terahertz (THz).

Various corrections may be used. Example corrections include: clipping correction, horizontal shift correction, attenuated total reflectance IR (ATR-IR) correction, vertical offset correction, and a baseline correction. These corrections can be applied to optimize the match between spectral curves. The corrections can be applied in combination with each other. Additional corrections, not mentioned herein, can also be applied.

I. SYSTEM

The spectra of a test sample and the reference samples can be obtained in any suitable manner, which can be as varied as the different spectrographic techniques. The analysis of the spectra can use any suitable computer (logic) system, e.g., a general purpose computer to an application specific circuit. An example system is described below.

FIG. 1 illustrates a system 100 for obtaining spectra and determining matching spectra according to embodiments of the present invention. As shown, system 100 includes a sample 105 (e.g., solvents, steroids, or industrial materials, such as paint or dyes) within a sample holder 110. Sample 105 can be of any type of substance of which a spectrum can be obtained, e.g., organic compounds and inorganic compounds, and can include mixtures.

A physical characteristic 115, such as a light intensity for various wavelengths, from the sample is detected by detector 120. In some embodiments, a light source (not shown) can transit light (e.g., infra-red light) over a range of wavelengths, and detector 120 can detect the intensity of light that is transmitted through the sample. In other embodiments, other devices may be used, e.g., other components of a mass spectrometer. In such a case, detector 120 could include other components besides a detector, e.g., components for preparing (e.g., ionizing and controlling molecules of the sample).

A detected signal 125 can be sent from detector 120 to logic system 130. Detected signal 125 can include electrical signals corresponding to intensity peaks at various wavelengths. Thus, signal 125 can be used to create a sample spectrum of sample 105. In one embodiment, an analog to digital converter can convert an analog signal to digital form, for processing by logic system 130. The analog to digital converter can be in detector 120 or in logic system 130, or between the two. The data from signal 125 may be stored in a local memory 135 or an external storage device 145.

Logic system 130 may be, or may include, a computer system, ASIC, microprocessor, etc. It may also include or be coupled with a display (e.g., monitor, LED display, etc.) and a user input device (e.g., mouse, keyboard, buttons, etc.). Logic system 130 and the other components may be part of a standalone or network connected computer system, or they may be directly attached to or incorporated in any detecting device. Logic system 130 may also include optimization software that executes in a processor 150 and that can implement methods described herein.

For IR spectroscopy, sample 105 is typically in liquid or a gaseous form. The resulting spectrum can be a curve. The sample holder can be a tube, and the sample can run through the tube. A light source can situated at a particular location with the detector situated on the opposite side of the tube. In various embodiments, the light source can provide a spectrum of light, where the detected signal can be deconvolved (e.g., using a Fourier transform) to determine intensity at any one wavelength, or the light source can rotate through wavelengths that are applied one at a time. Other configurations can be used, e.g., in ATR-IR.

Once a sample spectrum is obtained, processor 150 can compare the sample spectrum to any number of reference spectra stored in a reference spectra database 140. Reference spectra database 140 can include various numbers of reference spectra, e.g., 250,000, and all or a portion of the reference spectra can be compared to the sample spectrum. Reference spectra database 140 can include spectra of potentially of different types, such as transmission IR and ATR-IR.

II. OPTIMIZING CORRECTION VALUES

Typically, a sample spectrum would be corrected just once with predetermined values for correction parameters. This correction is done upfront before any comparison against reference spectra in a reference database. This one corrected sample spectrum would then be compared to the reference spectra to find matching spectra. As the correction is done before any comparison, the correction values might not be optimal. And, the correction values would be fixed for every comparison, which might cause poor matches for some reference spectra. Accordingly, determining the correction values upfront is a best guess for what correction values are good, but ultimately the upfront correction may not be very accurate across all of the reference spectra used. Further, the standard according to American Society for Testing and Materials (ASTM) is to correct only the sample spectrum, which can further limit the applicability of the one-time correction.

In contrast, embodiments are able to optimize the correction value(s) to get an optimized similarity score that provides a more accurate comparison of the two spectra. Default values for the correction parameters can be used, but the correction values would be dynamic and that they can iteratively change to provide an optimal similarity score. Optimal values for the correction parameters can be different for each pair of spectra. For example, the sample spectrum can be corrected in a different manner for one reference spectrum relative to another reference spectrum. To determine the optimal values, many comparisons may be performed between the two spectra, each comparison for a different set of correction values.

In this manner, an optimal correction for each pair spectra can be determined, thereby providing an optimal similarity score for any two spectra. And, the computer system can automatically determine which reference spectra are most similar to the sample spectrum. Since the similarity scores for determining an optimal manner, the identification of the most similar reference spectra can be more accurate. The final corrected spectra and must similar for a given pair spectra can be displayed for a user to visually inspect the similarities.

III. METHOD

Figure 2:
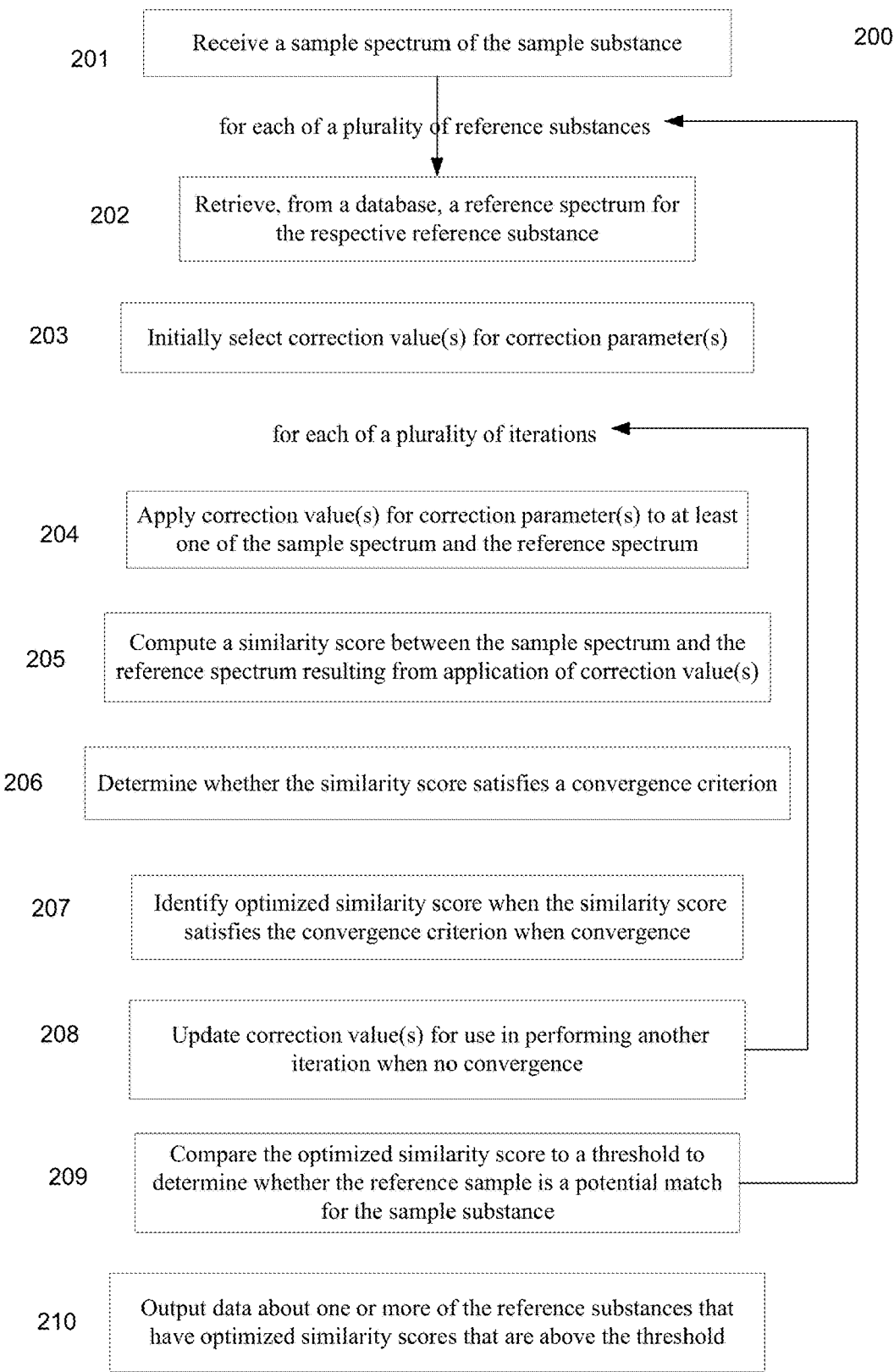
FIG. 2 is a flowchart of a method 200 for identifying a reference substance that matches a sample substance by comparing spectra.

FIG. 2 is a flowchart of a method 200 for identifying a reference substance that matches a sample substance by comparing spectra. All or a portion of method 200 can be performed by a computer system. The computer system can be attached to, part of, or otherwise in communication with a detector that can obtain a sample spectrum. For example, method 200 can be performed using all or parts of system 100.

At block 201, a sample spectrum of the sample substance is received. The sample spectrum can be received from a detector. The sample spectrum has an intensity value for each of a plurality of discriminating values of a discriminating property. The discriminating property can correspond to any physical property that underlies the spectrum. For example, mass, wavelength, or frequency are examples of the discriminating property. The sample spectrum can be received as a series of X-Y data points, e.g., an intensity value for each is committing value.

Blocks 202-209 can be performed for each of a plurality of reference substances. Each reference substance can have a corresponding reference spectrum, e.g., stored in a database. The operation of blocks 202-209 can be performed in parallel on different processors or threads for each different reference spectrum.

At block 202, for a respective reference substance, a reference spectrum is retrieved from a database for the respective reference substance. The reference spectrum has an intensity value for each of a plurality of discriminating values of a discriminating property. The sample spectrum and the reference spectrum can have more discriminating values than the plurality that are used for the comparison. The reference spectrum retrieved can be a next spectrum in a list.

At block 203, one or more correction values are initially selected for one or more correction parameters. Examples of correction parameters are provided in a following section. In some embodiments, just one correction value for one correction parameter may be used. In other embodiments, a plurality of correction values may be used, each correction value for a different correction parameter. In various embodiments, at least some initial values may be selected to provide no correction for a particular parameter or may be selected based on previous experience.

Blocks 204-208 can be performed for each of a plurality of iterations. The number of iterations can depend upon one or more convergence criteria. When the one or more convergence criteria are satisfied, the iterative loop can terminate.

At block 204, the one or more correction values for the one or more correction parameters are applied to at least one of the sample spectrum and the reference spectrum. In some embodiments, all of the correction values can be applied to the sample spectrum. In other embodiments, all the correction values can be applied to the reference spectrum. In yet another embodiment, some of the correction values can be applied to the sample spectrum and other correction values can be applied to the reference spectrum. In one aspect, one correction value may be applied to only one spectrum.

After applying the correction values, a corrected sample spectrum and/or a corrected reference spectrum can be obtained. Some correction values can be applied at the same time, e.g., for an ATR-IR conversion. One or other correction values can be applied independently of other correction values. The correction values can be applied sequentially or in parallel, with the condition of any correction values they need be applied together.

At block 205, a similarity score is computed between the sample spectrum and the reference spectrum resulting from application of the one or more correction values. For example, the similarity score can be between a corrected sample spectrum and the reference spectrum, between the sample spectrum and a corrected reference spectrum, or between a corrected sample spectrum and a corrected reference spectrum.

The similarity score can be determined based on differences between the intensity values at each discriminating value. These differences can individually or collectively be considered distances between the two spectra. Various techniques can be used to determine the total distance between the two spectra. For example, a Euclidean distance or a first derivative Euclidean distance can be used. The similarity score may be normalized to lie between zero and 100, or any two other numbers.

At block 206, it is determined whether the similarity score satisfies one or more convergence criteria. The convergence criteria may involve a comparison of the similarity score of one or more previous iterations with the similarity score of the current iteration. For example, once the similarity scores do not change more than a specified amount over a specified number of iterations (e.g., two or three), then the optimization of the correction values can be considered converged.

At block 207, when the similarity score satisfies the one or more convergence criteria, the current similarity score is identified as an optimized similarity score corresponding to one or more optimized values of the one or more correction parameters. The optimized values correspond to the correction values used to obtain the optimized similarity score.

At block 208, when the similarity score does not satisfy the one or more convergence criteria, the one or more correction values are updated for use in performing another iteration. The one or more correction values can be updated in a variety of way. For example, each correction value can be varied to determine an optimal value, with the other correction values fixed, as is described in more detail below. Accordingly, the optimal values of the one or more correction parameters can be determined sequentially, and the optimal value of a next correction parameter can be determined while keeping any previous correction parameters constant at a previously determined optimal value. In other embodiments, all or a portion of the correction values can be updated at a same time.

At block 209, the optimized similarity score is compared to a threshold to determine whether the reference sample is a potential match for the sample substance. The threshold can be specified in a variety of ways. For example, the threshold can correspond to the top N optimized similarity scores (or top X %), and thus block 209 may be performed after all of the optimized similarity scores are determined for the reference substances. The top N or top X % can encompass a rank of the optimized similarity scores. As another example, the threshold can be an absolute value for the optimized similarity score.

At block 210, data is output about one or more of the reference substances that have optimized similarity scores that are above the threshold. The data can be in various forms. As examples, the data can include an identifier for each of the corresponding reference substances. The data can include the optimized similarity scores themselves. The data can include the reference spectra (which may be corrected), each of which may be displayed in conjunction with the sample spectrum. In various embodiments, the data can be output by plotting curves of the sample spectrum and a first reference spectrum in an overlapping, stacked, or offset fashion using the one or more optimized values of the one or more correction parameters.

Accordingly, embodiments can perform matching of spectral data (e.g., curves). Embodiments can also be used to match curves of all types, for example, comparing the historic stock price chart of one company to another. To accomplish the matching, a curve (defined as a series of X-Y data points) can be compared to another curve in an iterative process.

IV. CORRECTION TYPES

Various correction parameters may be used. Multiple correction parameters may be of a same correction type, e.g., for ATR-IR conversion, and thus always be applied together. Other correction parameters can be applied independently. Some correction parameters would only be applied to a particular spectrum, e.g., a sample spectrum or a reference spectrum, while others can be applied to either (e.g., a baseline correction could be applied to either). And, some corrections may only be applied to one spectrum at most, e.g., a clipping correction, ATR-IR correction, and the vertical offset would typically only be applied to one spectrum.

If the correction parameter is not being used, the value can be set to zero or other value that provides no correction. The particular correction can also simply not be applied. The corrections can be applied to either the sample spectrum or the reference spectrum to which the sample spectrum is being compared. The similarity score is determined after any corrections have been applied.

A. Clipping Correction

According to ASTM's "Standard Guide for Use of Spectral Searching by Curve Matching Algorithms with Data Recorded Using Mid-Infrared Spectroscopy" E2310-04 (2009) section 5.1.1, for data pre-treatment to ensure that the Y-values of a reference spectrum curve and those of an unknown query spectrum curve have identical ranges, a normalization is performed: "Normalization of spectra compensates for the differences in sample quantity (concentration or pathlength, or both) used to generate the reference spectra in the library and that of the unknown." The paragraph further states: "If the range chosen for normalization has only one or two strong bands in the spectrum and a few medium intensity bands, the range of the spectrum must be reselected or the spectrum will be dominated by the strong bands in the spectrum and the HQI (hit quality index) will be insensitive to weaker fingerprint bands necessary for identification of a specific compound." Later, in section 7.4, the guide says that the normalization of spectra plays a key role in discriminating between similar spectra.

The industry standard practice of normalizing spectra for matching the spectrum curve of an unknown sample to the spectra of known reference compounds does not always produce optimal results. As the ASTM guide explains, smaller bands may be obfuscated by the search algorithm if the intensities of the largest peaks in the two spectra compared do not have identical Y-axis intensities. To overcome this problem, ASTM recommends that the largest peak or peaks be excluded from the search, but this method has two shortcomings: First, excluding the largest peaks causes their contribution to the hit quality value (an example of a similarity score) to become zero, which is not desirable. Second, if several large peaks exist in a spectral curve, deciding which should be excluded could become difficult if done manually.

In some embodiments, a clipping correction parameter can clip the largest peak(s) automatically while retaining their contribution to the hit quality value. The query spectral curve can be called curve Q while the library (reference) spectral curve can be called curve L. The clipping correction parameter specifies the largest contribution of any peak to the hit quality value. For example, if an intensity value at a particular discriminating value is above the clipping value, then calculation of the hit quality value will use the clipping value instead of the actual intensity value.

In a preprocessing step of an embodiment, a minimum intensity value in a spectrum can be subtracted from all intensity values in the spectrum. The resulting intensity values can then scaled by dividing the intensity values by the maximum intensity value in the spectrum. The result of these operations is a spectrum with intensity values that range from 0 to 1. If performed, this preprocessing step is applied to both curves Q and L.

The clipping correction is achieved by having all intensity values within a spectrum that lie above C truncated to the clipping value C. The clipping value C can be adjusted gradually, e.g., in iterations of method 200 or in subiterations to determine an optimal C with other correction parameters fixed. The hit quality value (HQV) can be established after every clipping operation to find the C for the best possible HQV. Any of the widely known search algorithms can be used to determine the HQV value, such as Euclidean distance or first derivative Euclidean distance. In various embodiments, the process can be repeated with changing curve Q while holding curve L constant or with changing curve L while keeping curve Q constant. It may be necessary to clip peaks either in curve Q or in curve L to receive the best HQV.

In some embodiments, an optimal C is found by use of a binary algorithm. A minimum allowed C of ⅓ (or other values) can be used, because smaller clipping values may cause spectral matches to be found that do not make sense. The HQVs for the following values of C can be calculated: 1, $3^{-1/4}$, $3^{1/2}$, $3^{-3/4}$, and $3^{-1}$. If any other correction parameters are used, their values can be kept constant, e.g., at a previously determined optimal value. The value of C with the best HQV is used as the starting point for the following binary approximation algorithm.

The preceding and following C values define an interval that is cut in half. The HQV of the midpoint of every one of the two half intervals is calculated. The better HQV value defines the half interval to be used as the interval for the next cutting step. The process is repeated until the interval becomes very small (e.g. $10^{-7}$), which corresponds to an example of a convergence criterion. If the resulting C value is very close to the minimum permissible value of ⅓, the clipping optimization can be assumed to have failed. The resulting optimal C value defines a clipping region of the curve that will not contribute to the HQV (unless C is found to be exactly 1).

This resulting optimal C value can be performed as part of block 208 of method 200. Each of the correction parameters can be updated in this manner, e.g., while the other correction parameters are kept fixed. The other correction parameters can be kept fixed at the values determined in a previous iteration. Each iteration of method 200 can involve determining new value(s) of correction parameter(s) in this manner.

B. Horizontal Shift Correction

Due to differences in the way spectra are collected on instruments, it is possible that Q and L are not perfectly aligned horizontally, even if Q and L were collected from exactly the same substance. The following equation can be used to determine a corrected discriminating value: $v_{corr}=v+H$, where the horizontal shift parameter H shifts the discriminating parameter v (e.g., wavelength) so that an X-Y data point has a new X value. In some implementations, the horizontal shift parameter H may range from −3 to 3 $cm^{-1}$. Embodiments can determine an optimal value for the correction parameter H in a binary algorithm as described above for the clipping parameter. The value of H with the best HQV is assumed to describe the horizontal shift best.

C. ATR-IR Correction

Infrared (IR) spectra can be measured via the amount of IR radiation that is transmitted through a sample (Transmission IR) or via the amount of IR radiation that is attenuated when it is reflected off a sample (Attenuated Total Reflectance IR, or ATR-IR). Thus, there are two different types of spectra. One type produces transmission IR spectra, e.g., using Fourier transform infrared spectroscopy (FTIR), and the type produces ATR-IR spectra. The spectra are slightly different, and thus cannot be compared directly to each other. For example, the peaks are slightly different, the intensities are slightly different, and there is a shift on the X-axis. But, the spectra from the two types can be compared after a correction is performed. Allowing a comparison between the two types of spectra allows for a larger set of reference spectra to be searched to find a match. The ATR-IR is cheaper to produce currently, and thus there are more ATR-IR spectra now. Historically, there is more transmission IR data, and thus the conversion is often performed on an ATR-IR sample spectrum to a transmission IR spectrum.

However, it is not easy to select good correction values for the conversion. A determination of optimal correction parameters for the conversion by optimizing an HQV can provide good correction values. In this manner, an optimized, individual conversion can be performed for each pair of spectra.

In more detail, a wavelength-dependent change in Y-Axis absorption occurs when comparing ATR-IR and transmission IR spectra, but a commonly-used mathematical correction function allows an ATR-IR spectrum to be made comparable to a transmission IR spectrum so that traditional spectral curve matching algorithms can be used. When comparing an ATR-IR spectrum against a transmission IR spectrum or vice versa, therefore, the resulting HQV will be poor until the correction function is applied to convert one into the other. Several methods exist for the conversion taking various parameters into account such as the penetration depth, the refractive indices of the crystal and the sample, and the angle of incidence.

Unfortunately, these parameters may not be available when the search is performed. A qualitative method that works reasonably well is to use the following conversion function: $I_C=I \cdot (1+(v-v_0)/v_0)$, where $I_C$ is the corrected intensity, I is the original intensity, v is the wavenumber of the data point, and $v_0$ is the wavenumber of the first data point in the spectrum, which is an example of a first discriminating value of a first data point. Experience has shown that the conversion function above needs to be modified by introducing a peak intensity shift F: $I_C=I \cdot (1+F \cdot (v-v_0)/v_0)$.

Reasonable values of F appear to lie within ⅔ and ¾. Anything outside this range can indicate that there is a problem that may lead to incorrectly assigned spectra. As described above, embodiments can find an optimal factor F, e.g., using a binary algorithm. The value of F with the best HQV is assumed to describe the best ATR-IR correction.

In addition to a peak intensity shift, embodiments can also use a horizontal shift towards lower wavenumbers that is not constant but depends on maximum peak intensities. An improved correction of the X axis shift can take this into account. The higher a peak, the more it is shifted. Unfortunately, a thorough determination of all peaks in a spectrum would require spectral deconvolution, and the necessary processing time to accomplish this makes it difficult to be used during a spectral data search where potentially hundreds of thousands of spectra are to be compared. A simpler approach determines peak clusters that are separated from other clusters enough to let the intensity values fall below a certain threshold between clusters.

Embodiments can use a minimum intensity threshold of 4%. The maximum intensity value k within each cluster can be used for the X axis corrections of all intensity values within that cluster in the following way: $v_{corr}=v+H \cdot h_c$. As examples, the horizontal shift parameter H applied during an ATR correction may range from 0 to 10 $cm^{-1}$. In some implementations, spectral regions with intensity values below the minimum intensity threshold are not shifted horizontally.

If an ATR-IR correction is performed using the above horizontal shift parameter H, then a horizontal shift described in section IV.B would not be performed. Further, one value of H can be used for all clusters. The actual horizontal shift varies by cluster in that the maximum intensity value $h_c$ (which varies) within each cluster is used to determine how much to shift that cluster.

In addition to the variations in intensities corrected by the parameter F described above, there are non-polarization effects that may cause the tops of higher peaks to be different between Q and L. To compensate for these variations, the following equation introduces a polarization adjustment parameter P and is applied to all intensity values that lie above a specified portion (e.g., 50%) of the maximum intensity of the spectrum: $I_C=0.5+(I-0.5)\cdot(1-(1-P)\cdot h_c)$, where $h_c$ is the maximum intensity value within each cluster. Example values of P are assumed to be within ⅓ and 1. Embodiments can determine the parameter P in a binary optimization process, as described further. The value of P with the best HQV is assumed to describe the non-polarization effect best. Intensity values above a specified amount are reduced for a cluster of discriminating values based on P, where the reduction proportional to a maximum intensity of the cluster. The parameters F, H, and P can be optimized independently, e.g., as are parameters of other corrections.

D. Vertical Offset Correction

Similar to a potential horizontal shift between Q and L, the baselines of Q and L may not be perfectly aligned. This effect can be caused by small downward spikes or jitter in the baseline, for example. In the following equation $I_C=I+V$, the intensity is corrected by a vertical offset. Thus, all of the intensities would be shifted by a fixed amount. As examples, the vertical offset parameter V may range from −0.07 to 0.07 (−7 to 7%). Embodiments can apply the factor V in a binary algorithm, as described above. The value of V with the best HQV can be assumed to describe the vertical offset best. The vertical offset parameter V can be used in conjunction with an ATR-IR conversion correction.

E. Baseline Correction

A good baseline can be important for any spectral comparison that uses Euclidean or Euclidean correlation algorithms to determine an HQV. Often, it is not easy to determine exactly where the baseline should be, particularly when larger peaks rarely let the spectrum fall back to its natural baseline. The baseline correction can fix a slant in the baseline, whereas the vertical offset can dynamically move the spectrum vertically until the best HQV is achieved. In some implementations, the baseline correction is a static (one-time, yes or no) operation while the vertical offset is optimized dynamically.

Some embodiments can apply a baseline correction to both Q and L, running all the calculations mentioned above to produce four different HQV values in the following combinations: Q versus L, Q (baseline corrected) versus L, Q versus L (baseline corrected), and Q (baseline corrected) versus L (baseline corrected). The best HQV value from the four options is assumed to describe the necessary baseline correction(s) best. The baseline correction itself is an automatic algorithm that tries to find points in the baseline and connects them through lines. The intensity values of the spectrum are then subtracted by the intensity values of the lines to produce the corrected spectrum. Any suitable automatic baseline correction algorithm may be used, as would be known to one skilled in the art, e.g., as described in Lan et al., "Automatic baseline correction of infrared spectra," Chinese Optics Letters, Vol. 5, No. 10, Oct. 10, 2007; and Yu et al., "A New Approach For Spectra Baseline Correction Using Sparse Representation," IASTED International Conference on Signal Processing, Pattern Recognition and Applications (SPPRA), 2013, which are incorporated by reference.

In other embodiments, the baseline correction can be determined in a same way as the other correction parameters, e.g., by determining an optimal value in an inner loop while keeping the other correction parameters fixed. The correction parameters at the end of the inner loops can then be used to determine an HQV that is compared to a previous HQV value in the outer loop.

For example, embodiments can apply a linear baseline correction function in the shape of: $I_C=I-B\cdot(v_0-v)/(v_1-v_0)$ or $I_C=I-B\cdot(v-v_1)/(v_1-v_0)$, where $v_1$ is the wavenumber of the last data point in the spectrum, and B is a baseline adjustment factor that is iteratively optimized. It can be assumed that the maximum intensity value in the spectrum is 1. The first function causes a baseline to be fixed that slopes downwards from left to right while the latter fixes upward slopes. Which of the two functions works best can be determined by applying the same binary algorithm as described above. The value of B with the best resulting HQV is considered to describe the baseline most appropriately. Experience has shown that reasonable values of B lie between 0 and 0.2. Various other functions could be used, such as linear functions, polynomial functions, manual point determination, or automatic point determination.

V. UPDATING CORRECTION VALUES FOR A NEXT ITERATION

The correction parameters can be combined to result in a set of correction values. For example, five individual iteratively optimized corrections C, H, F, P, and V can be combined to result in a set of values that describe the necessary pre-processing of curve Q to provide the best possible HQV. Embodiments can further include B (or other parameters not mentioned herein), or include less parameters.

As mentioned above, an embodiment can first determine an initial similarity score using default values. For example, the HQV can be computed for the default values (1, 0, 1, 1, and 0) of C, H, F, P, and V. Then, the correction values can be updated to obtain a new set of correction values to an updated similarity score, which can be compared against the previous similarity score (initial for the first iteration). If the updated similarity score is better than the previous similarity score, then the updated correction values can be accepted. The steps can be repeated until the difference between the previous and updated HQV becomes minimal (e.g. $10^{-7}$). These steps can be part of an outer loop.

The updated set of correction values can be determined in a variety of ways. In some embodiments, all of the correction values can be updated at a same time and an updated similarity score computed, without computing any intermediate similarity scores. In other embodiments, each correction parameter of the set can be optimized separately via an inner loop, with intermediate similarity scores being determined as part of the optimization of the particular correction parameter. The update of the entire set for the outer loop can be the optimal correction values obtained at the end of the separate optimization for each of the correction parameters, as is described in the next section. In yet another embodiment, a subset of correction parameters can be updated together (e.g., parameters for ATR correction) and separate from another correction parameter outside the subset.

A. Cycling Through Each Correction Parameter

As mentioned above, the update of the set of correction parameters can involve separate optimizations of each correction parameter. Thus, after the initial similarity score is determined, a first correction parameter can be varied to determine an optimal value, at least optimal given the default values of the other correction parameters. As part of determining the optimal value, similarity scores can be computed for various values of the first correction parameter, and an optimal similarity score can be determined, e.g., using the binary algorithm described above. Once an optimal value for the first correction parameter is determined, then an optimal value for a second correction parameter can be determined, e.g., using the optimal value previously determined for the first correction parameter.

Accordingly, the optimal value for a first correction parameter can be determined in the following manner. For each of a plurality of subiterations, the similarity score can be computed between the sample spectrum and the reference spectrum resulting from application of a set of correction values (i.e., the set for all of the correction parameters) at each of a plurality of correction values of the first correction parameter. Thus, multiple sets of correction values can be used, with sets differing just by having different values for the first correction parameter. A top similarity score at the sets of correction values can be identified. Whether the top similarity score satisfies one or more other convergence criteria can be determined. When the top similarity score satisfies the one or more other convergence criteria, the value for the first correction parameter can be identified as the optimal value for the first correction parameter. When the top similarity score does not satisfy the one or more other convergence criteria, new correction values can be determined for a next subiteration based on the set of correction values corresponding to the top similarity score.

For example, if the method starts with a clipping correction, embodiments can adjust the clipping parameter until the HQV is best. This adjusting can be done in subiterations that can be performed in an inner loop for each correction parameter. And then, the process can proceed to the next parameter, e.g., for the ATR correction parameters. So now, the process can adjust a first ATR correction parameter until the match becomes best again. The process can proceed to do this on all the different correction parameters until a complete, updated set is obtained. This can mark an end of one iteration of an outer loop.

A similarity score can then be determined for the updated set (e.g., as the similarity score of the optimal value for the last correction parameter). After the updated set of correction parameters is obtained, a next iteration of the outer loop can be performed by optimizing the clipping correction, using the optimal values of the other correction parameters obtained from the previous iteration of the outer loop. The iterations of this loop can be performed as many times as is necessary to obtain convergence, e.g., the similarity score does not change appreciably from one iteration to another. Thus, one can obtain a final best similarity score for the given pair of spectra, namely for one particular query spectrum, and one particular library spectrum.

B. Determining Optimal Value for One Correction Parameter

As mentioned above, the determination of an optimal value of a correction parameter can be done one correction parameter at a time in an inner loop. This optimization can use a binary search algorithm. For example, an embodiment can select five different values for a correction parameter at the beginning and calculate all HQVs for those. The two best sequential HQVs can be determined and used to define the interval of the correction parameter to investigate further.

The new, smaller interval can be cut in half, with a new correction value at the midpoint, and two other new values at ¼ and ¾ of the interval. Similarity scores can be determined for the three new values of the correction parameter. The two best sequential HQVs can be determined again, and intervals cut in half again until the final HQV does not improve by more than a specified convergence criterion (e.g., 1e-7). The other parameters can be optimized in the same way.

C. Similarity Score (HQV)

The similarity score can be determined in various ways. For example, the similarity score can be determined as a distance between the two spectra, with the differences between corresponding intensity values (i.e., at same discriminating value) used to determine the difference. Thus, each of the two spectra can be defined as N data points, and the distance between these points can be determined.

One technique is a Euclidean distance algorithm. To determine the distance, one embodiment calculates the product of every two intensity values. For example, if there is a query Q and a reference R, then the product of each $Q_1$ and $R_1$ values can be determined (e.g., each of the two corresponding values are multiplied). The products are added together to obtain a sum of these multiplications. Thus, the dot product of the two spectral curves Q·R (which is the product of the norms) can be determined in this manner. The square norm $\|Q\|^2$ of the first spectrum of the query will be the sum of the $Q_1$ values squared. And, the square norm $\|R\|^2$ of the reference spectrum will be the sum of the $R_1$ values squared. The distance can then be calculated as $\sqrt{\|Q\|^2+\|R\|^2-2Q\cdot R}$. The result can be normalized by dividing by either norm, e.g., $$\frac{\sqrt{\|Q\|^2 + \|R\|^2 - 2Q\cdot R}}{\|Q\|^2}.$$

For this distance, zero is a perfect match, and one means not a match at all. This zero to 1 range can be converted into other ranges, e.g., a zero to 100 range or zero to 99 range.

VI. DISPLAYING TOP MATCHING SPECTRA

As described for method 200, optimized correction values can be obtained for each pair of spectra, e.g., the sample spectrum with each reference spectrum of a library. A similarity score can also be obtained for each pair. Thus, one can obtain an optimized HQV for every library spectra. The top HQVs can be provided to a researcher, e.g., the top 10 or top 10%.

In addition to the list of the top N matches (or top N % matches), embodiments can provide visual feedback to the user of what was corrected. The baseline correction, as an example, could be described by showing the original spectrum without the baseline correction, and the baseline corrected one. Or, the clipping correction could be shown by displaying a horizontal line showing where the peaks were clipped.

The two spectra (after any correction) can be displayed together. The calculated parameters C, H, F, P, and V, as well as the decision on the baseline correction(s), can be used to alter curves Q and L such that the user gets the best possible feedback on exactly what data was fed to the spectral comparison algorithm. In most cases, a good HQV will also result in visually matching spectral curves.

If the spectral comparison algorithm was Euclidean or Euclidean correlation, curve Q can be scaled according to the Euclidean norms of both spectra. The Euclidean norm of a spectrum P is defined as $$\|P\|=\sqrt{p_1^2+p_2^2+\ldots+p_n^2}=\sqrt{P\cdot P}.$$

Curve Q can be multiplied (scaled) by $P_L/P_Q$ in order to appear exactly like the comparison algorithms "see" the input data. This final scaling can be done before or after application of any correction parameters. In this manner, the spectra can be displayed in a suitable manner to visually compare them to each other.

The order for applying the correction parameters can vary. In one embodiment, the order for the correction parameters can be baseline first, ATR correction next, clipping correction, followed by a vertical offset.

VII. EXAMPLES

Below are example comparisons of spectra using predetermined correction values and optimized correction values. As can see from the examples, there is a significant difference to the human eye.

A. Clipping Correction

For the clipping correction, two spectra of a same substance are compared. For example, two spectra of 2-Furaldehyde are compared to each other. Also, two spectra of anisole are compared to each other. Thus, the following examples demonstrate the iteratively optimized clipping correction and corresponding display.

FIG. 3A shows an original result of 2-Furaldehyde with match score of 87.6%. FIG. 3A shows the resulting display of a search spectrum 310 of 2-Furaldehyde (black) compared with the reference spectrum 305 (red) of the same compound. Using the correlation algorithm to determine a similarity score and industry standard normalization, an HQV of 87.6% is obtained. As one can see, the heights of many peaks differ, except for the highest peak. Further, the decay from a peak is often faster for search spectrum 310.

FIG. 3B shows an iteratively optimized clipping correction and display result of 2-Furaldehyde with match score of 96.2% according to embodiments of the present invention. FIG. 3B shows the resulting display of a search spectrum 320 of 2-Furaldehyde (black) compared with the reference spectrum 315 (red) of the same compound. Using only the iteratively optimized clipping correction, an HQV of 96.2% is obtained.

Dotted line 325 expresses the vertical location where spectral clipping was performed, namely what the optimal value for the clipping parameter was determined to be. Only those parts of the spectrum that lie above the dotted line 325 are omitted from the search. The major part of the largest peak(s) is still taken into account by the search algorithm. As one can see, the heights of most of the peaks of search spectrum 330 are commensurate with reference spectrum 315, except for the highest peak, whose value has been clipped.

Typically, people would eliminate a specific peak. Thus, the entire peak would be excluded from being searched. For clipping, instead of eliminating entire peaks, only the tops of peaks are ignored when determining the optimal correction parameters and a similarity score. The further dotted line 325 is toward the bottom, more and more top portions of peaks are excluded. Any intensity value that is above the horizontal line would be set back to the value at the horizontal line, i.e., clipped, when determining a similarity score.

FIG. 3C shows iteratively optimized corrections and display result of 2-Furaldehyde with match score of 97.6% according to embodiments of the present invention. FIG. 3C shows the resulting display of a search spectrum 340 of 2-Furaldehyde (black) compared with the reference spectrum 335 (red) of the same compound. Using the iteratively optimized corrections of C, H (section IV.B), and V, an HQV of 97.6% is obtained. Dotted line 345 expresses the vertical location where spectral clipping was performed.

FIG. 4A shows an original result of Anisole with match score of 87.8%. FIG. 4A shows the resulting display of a search spectrum 410 of Anisole (black) compared with the reference spectrum 405 (red) of the same compound. Using the correlation algorithm and industry standard normalization, an HQV of 87.8% is obtained. As one can see, the heights of many peaks differ, except for the highest peak. Further, the decay from a peak is often faster for search spectrum 410.

FIG. 4B shows an iteratively optimized clipping correction and display result of Anisole with match score of 95.4% according to embodiments of the present invention. FIG. 4B shows the resulting display of a search spectrum 420 of Anisole (black) compared with the reference spectrum 415 (red) of the same compound. Using the iteratively optimized clipping correction, an HQV of 95.4% is obtained. Dotted line 425 expresses the vertical location where spectral clipping was performed. As one can see, the heights of most of the peaks of search spectrum 420 are commensurate with reference spectrum 415, except for peaks whose value has been clipped.

FIG. 4C shows iteratively optimized corrections and display result of Anisole with match score of 97.6% according to embodiments of the present invention. FIG. 4C shows the resulting display of a search spectrum 440 of Anisole (black) compared with the reference spectrum 435 (red) of the same compound. Using the iteratively optimized corrections of C, H (section IV.B), and V, an HQV of 97.6% is obtained. Dotted line 445 expresses the vertical location where spectral clipping was performed.

B. ATR Correction

The following examples demonstrate the iteratively optimized ATR-IR correction and corresponding display.

Figure 5A:
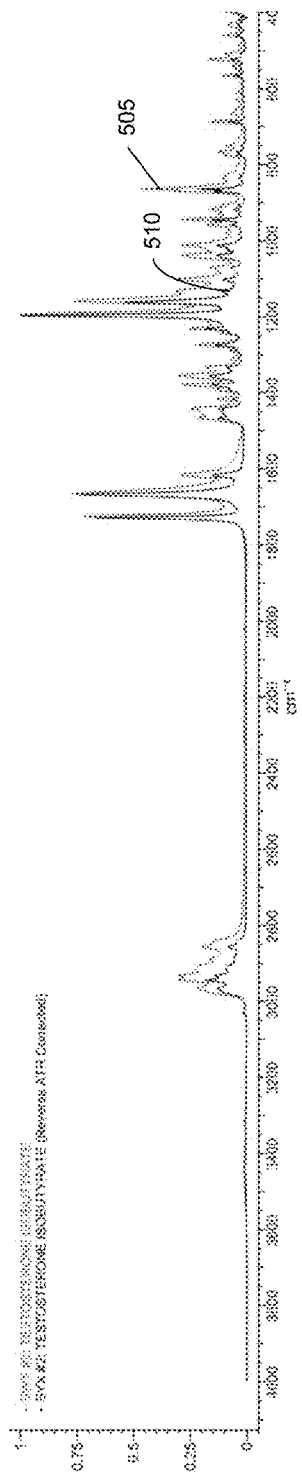
FIG. 5A shows an original result of Testosterone Isobutyrate with HQV of 79.8% according to embodiments of the present invention.

FIG. 5A shows an original result of Testosterone Isobutyrate with HQV of 79.8% according to embodiments of the present invention. FIG. 5A shows the resulting display of a search spectrum 510 of Testosterone Isobutyrate (black) compared with the reference spectrum 505 (red) of the same compound. Using the correlation algorithm and industry standard normalization, an HQV of 79.8% is obtained. Thus, the match starts out quite poor.

Figure 5B:
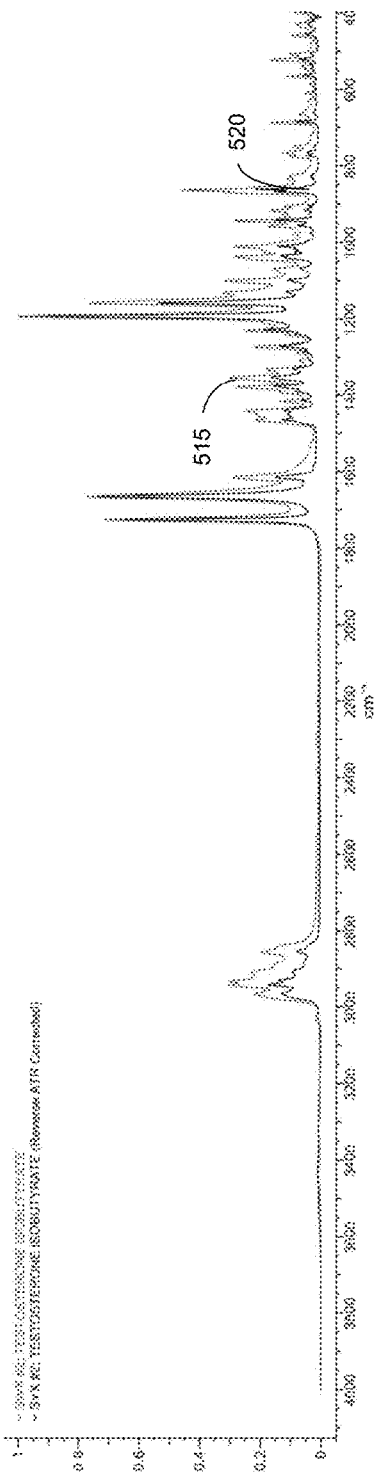
FIG. 5B shows an iteratively optimized ATR Correction result of Testosterone Isobutyrate with HQV of 90.4% according to embodiments of the present invention.

FIG. 5B shows an iteratively optimized ATR Correction result of Testosterone Isobutyrate with HQV of 90.4% according to embodiments of the present invention. FIG. 5B shows the resulting display of a search spectrum 520 of Testosterone Isobutyrate (black) compared with the reference spectrum 515 (red) of the same compound. Using only the iteratively optimized ATR-IR Correction, an HQV of 90.4% is obtained. Thus, the match has improved significantly, although one can still see significant different between the two spectra.

Figure 5C:
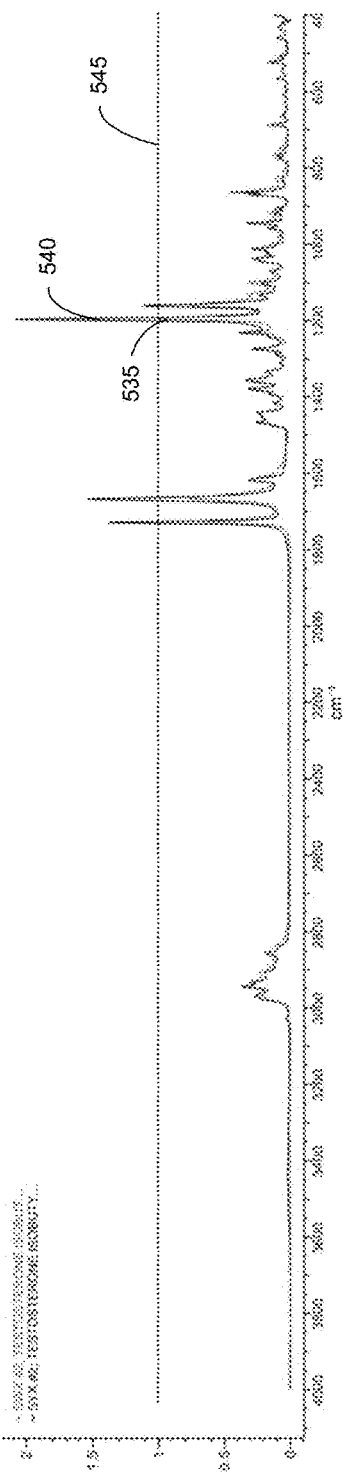
FIG. 5C shows an iteratively optimized correction and display result of Testosterone Isobutyrate with HQV of 97.0% according to embodiments of the present invention.

FIG. 5C shows an iteratively optimized correction and display result of Testosterone Isobutyrate with HQV of 97.0% according to embodiments of the present invention. FIG. 5C shows the resulting display of a search spectrum 540 of Testosterone Isobutyrate (black) compared with the reference spectrum 535 (red) of the same compound. Using the iteratively optimized corrections of C, F, H (section IV.C), P, and V, an HQV of 97.0% is obtained. Dotted line 545 expresses the vertical location where spectral clipping was performed. With all of the iteratively optimized corrections, the match improves dramatically.

C. Baseline Correction

The following examples demonstrate the iteratively optimized baseline correction and corresponding display. The baseline correction was applied to either query spectrum, reference spectrum, both, or none to produce four cases. For every one of these cases, the parameters are iteratively optimized. The case with the best HQV is finally used.

FIG. 6A shows an original result of 3,4,3',4'-Biphenyltetracarboxylic 3,4:3',4'-dianhydride with HQV of 57.9%. FIG. 6A shows the resulting display of a search spectrum 610 of 3,4,3',4'-Biphenyltetracarboxylic 3,4:3',4'-dianhydride (black) compared with the reference spectrum 605 (red) of the same compound. Using the correlation algorithm and industry standard normalization, an HQV of 57.9% is obtained. As one can see, the match is quite poor. In particular, the region on the left has the search spectrum 610 visibly higher than the reference spectrum 605, due to baseline error. Such a difference would likely not identify a possible match between the two spectra.

FIG. 6B shows a baseline correction result of 3,4,3',4'-Biphenyltetracarboxylic 3,4:3',4'-dianhydride with HQV of 83.7% according to embodiments of the present invention. The baseline correction was applied to the query spectrum. FIG. 6B shows the resulting display of a search spectrum 620 of 3,4,3',4'-Biphenyltetracarboxylic 3,4:3',4'-dianhydride (black) compared with the reference spectrum 615 (red) of the same compound. Using only the baseline correction, an HQV of 83.7% is obtained. As one can see, the baseline error has been reduced dramatically.

FIG. 6C shows an iteratively optimized correction and display result of 3,4,3',4'-Biphenyltetracarboxylic 3,4:3',4'-dianhydride with HQV of 89.4% according to embodiments of the present invention. FIG. 6C shows the resulting display of a search spectrum 640 of 3,4,3',4'-Biphenyltetracarboxylic 3,4:3',4'-dianhydride (black) compared with the reference spectrum 635 (red) of the same compound. Using the iteratively optimized corrections of C, H (section IV.B), and V, and using a baseline correction applied to the query spectrum, an HQV of 89.4% is obtained. Dotted line 645 expresses the vertical location where spectral clipping was performed. With all of the iteratively optimized corrections, the two spectra visibly match.

D. Abalyn

The following examples demonstrate the iteratively optimized correction and corresponding display for Abalyn. The results show that an incorrect match would have been identified with the original result, while a correct match is identified for the iteratively optimized correction.

FIG. 7A shows an original result for an Abalyn Sample with HQV of 79.3% according to embodiments of the present invention. An HQV of 79.3% was obtained for a comparison to the Abalyn reference spectrum. The 79.3% for HQV was lower than the 50$^{th}$ result for other substances, which is lower than a spectroscopist would identify as a potential match. Thus, an incorrect identification of the reference substance would be obtained using the original result.

FIG. 7B shows an iteratively optimized result for an Abalyn Sample with HQV of 98.3% according to embodiments of the present invention. With the optimized values for the clipping correction, horizontal shift, and vertical offset, the comparison to the Abalyn reference spectrum provides a 98.3% HQV, which is the first match in the resulting list. Thus, a correct identification of the substance is obtained. In this example, the optimized values for the corrections were as follows: (1) The top 44.0% of the query spectrum was clipped; (2) The query spectrum was offset horizontally by −10.5 cm-1; and (3) The query spectrum was offset vertically by 1.2%.

VIII. COMPUTER SYSTEM

Figure 8:
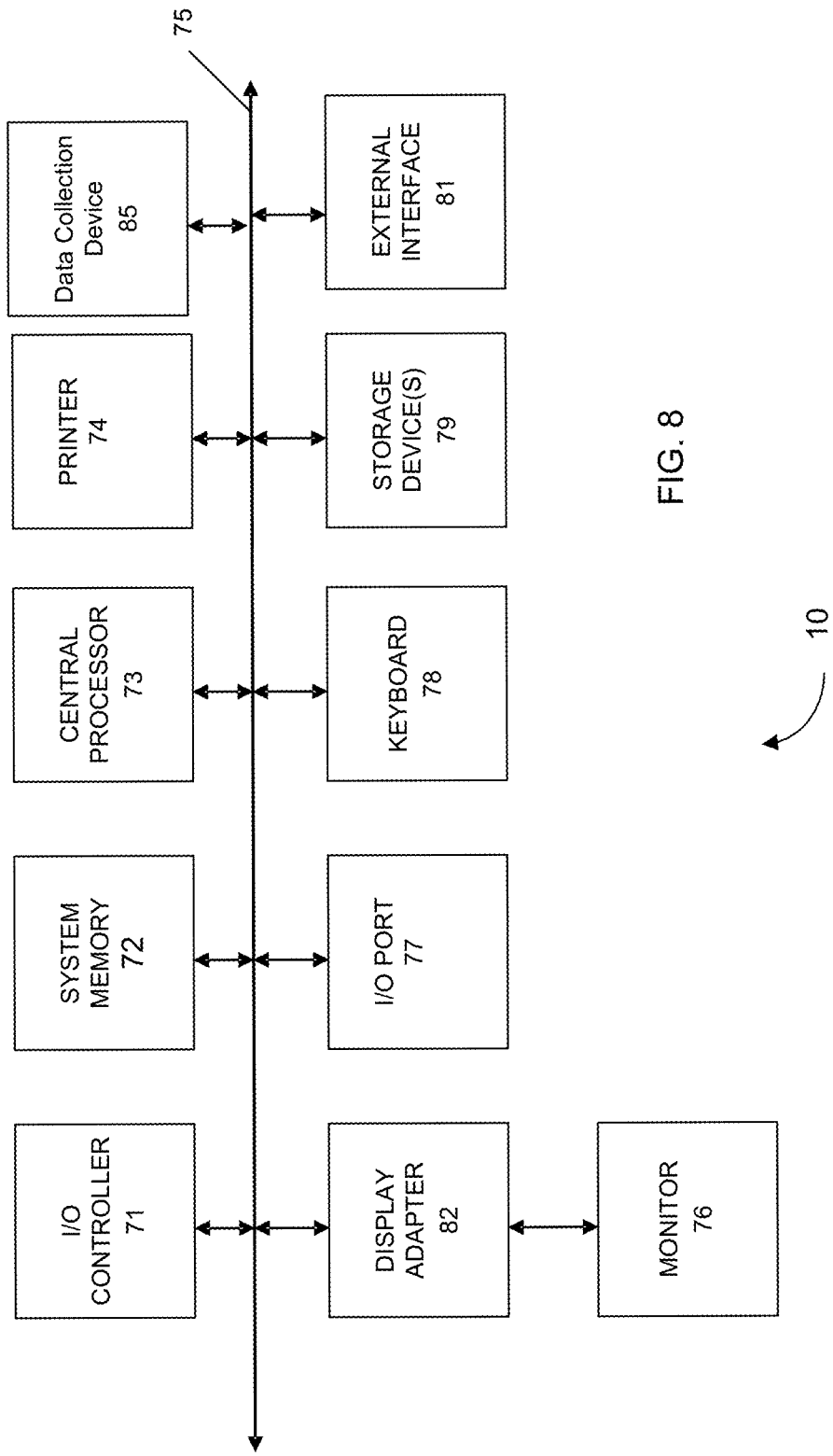
FIG. 8 shows a block diagram of an example computer system 10 usable with system and methods according to embodiments of the present invention.

Any of the computer systems mentioned herein may utilize any suitable number of subsystems. Examples of such subsystems are shown in FIG. 8 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 8 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method for identifying one or more substances in a sample, the method comprising performing, by a computer system:

shining a light beam on the sample;

measuring a sample spectrum of the sample by detecting light transmitted or reflected by the sample using a detector, the sample spectrum having an intensity value for each of a plurality of wavelengths;

for each of a plurality of reference substances:

retrieving, from a database, a reference spectrum for the respective reference substance, the reference spectrum having intensity values for the plurality of wavelengths;

initially selecting one or more correction values for one or more correction parameters to be applied to at least one of the sample spectrum and the reference spectrum, the one or more correction parameters corresponding to at least one of a clipping correction, a horizontal shift correction, a vertical offset correction, or a baseline correction;

for each of a plurality of iterations:

applying the one or more correction values for the one or more correction parameters to at least one of the sample spectrum and the reference spectrum;

computing a similarity score between the sample spectrum and the reference spectrum resulting from application of the one or more correction values, the similarity score determined using differences between the intensity values of the reference spectrum and corresponding intensity values of the sample spectrum;

determining whether the similarity score satisfies one or more convergence criteria;

upon determining that the similarity score satisfies the one or more convergence criteria, identifying the similarity score as an optimized similarity score corresponding to one or more optimized values of the one or more correction parameters; and upon determining that the similarity score does not satisfy the one or more convergence criteria, updating the one or more correction values for use in performing another iteration until the similarity score satisfies the one or more convergence criteria; and comparing the optimized similarity score to a threshold to determine whether the sample contains the reference substance; and outputting data about one or more of the plurality of reference substances that have optimized similarity scores that are above the threshold.

2. The method of claim 1, wherein the one or more correction parameters are a plurality of correction parameters, thereby providing a set of corrections values, and wherein updating the one or more correction values for use in performing the other iteration includes:

for each correction parameter of the plurality of correction parameters:

determining an optimal value for the correction parameter while keeping other correction values fixed, wherein the optimal value is based on optimizing the similarity score; and updating the plurality of correction values to have the optimal values.

3. The method of claim 2, wherein the optimal values of the one or more correction parameters are determined sequentially, and wherein the optimal value of a next correction parameter is determined while keeping any previous correction parameters constant at a previously determined optimal value.

4. The method of claim 2, wherein the plurality of corrections parameters includes a first correction parameter, and wherein determining the optimal value for the first correction parameter includes:
for each of a plurality of subiterations:
computing the similarity score between the sample spectrum and the reference spectrum resulting from application of the set of correction values at each of a plurality of correction values of the first correction parameter;
identifying a top similarity score at the sets of correction values;
determining whether the top similarity score satisfies one or more other convergence criteria;
when the top similarity score satisfies the one or more other convergence criteria, identifying the value for the first correction parameter as the optimal value for the first correction parameter; and
when the top similarity score does not satisfy the one or more other convergence criteria, determining new correction values for a next subiteration based on the set of correction values corresponding to the top similarity score.

5. The method of claim 1, wherein the one or more correction parameters include a clipping parameter that specifies a maximum intensity value at any wavelength of one of the sample spectrum or the reference spectrum to be used when computing the similarity score.

6. The method of claim 1, wherein the one or more correction parameters include at least one of: a horizontal shift correction parameter and a vertical offset correction parameter.

7. The method of claim 1, wherein the one or more correction parameters include a plurality of conversion correction parameters for converting a transmission IR spectrum to an attenuated total reflectance IR spectrum or converting an attenuated total reflectance IR spectrum to a transmission IR spectrum.

8. The method of claim 7, wherein the plurality of conversion correction parameters include a polarization adjustment parameter P that reduces intensity values above a specified amount for a cluster of wavelengths, wherein the intensity values of the cluster of wavelengths are reduced by a factor that is proportional to a maximum intensity of the cluster of wavelengths.

9. The method of claim 8, wherein the polarization adjustment parameter P is used to performed a correction of an intensity I at a particular wavelength using
$I_C = 0.5 + (I - 0.5) \cdot (1 - (1-P) \cdot h_c)$, where $I_C$ is a corrected intensity, and $h_c$ is a maximum intensity value within a cluster that includes the particular wavelength.

10. The method of claim 7, wherein the plurality of conversion correction parameters include a horizontal shift parameter H that is applied to a wavelength v using $v_{corr} = v + H \cdot h_c$, wherein $v_{corr}$ is a corrected wavelength, and wherein $h_c$ is a maximum intensity value within a cluster that includes the wavelength.

11. The method of claim 7, wherein the plurality of conversion correction parameters include a peak intensity shift F that is applied an intensity I at a particular wavelength v using equation $IC = I \cdot (1 + F \cdot (v - v_0)/v_0)$, wherein $I_C$ is a corrected intensity, and $v_0$ is a first wavelength of a first data point in a spectrum to which the plurality of conversion correction parameters are applied.

12. The method of claim 1, further comprising:
for a first reference spectrum of a first reference substance of the plurality of reference substances:
performing a baseline correction to at least one of the sample spectrum and the first reference spectrum, prior to the plurality of iterations.

13. The method of claim 12, further comprising:
determining four respective optimized similarity scores for a first reference spectrum corresponding to four options of applying the baseline correction to only the sample spectrum, to only the first reference spectrum, to both the sample spectrum and the first reference spectrum, and not applying the baseline correction to either the sample spectrum or the first reference spectrum; and
using a highest of the four respective optimized similarity scores as the optimized similarity score for the first reference spectrum.

14. The method of claim 1, wherein the threshold is one of: an absolute number and a rank of the similarity scores.

15. The method of claim 1, wherein outputting the data about the one or more of the reference substances includes:
plotting curves of the sample spectrum and a first reference spectrum in an overlapping, stacked, or offset fashion using the one or more optimized values of the one or more correction parameters.

16. The method of claim 1, wherein the light beam comprises one of infra-red light, ultraviolet light, visible light, X-ray light, or terahertz light.

17. A computer product comprising a non-transitory computer readable medium storing a plurality of instructions, that when executed on one or more processors of a computer system coupled to a light source and a detector, causing the computer system to perform:
shining a light beam emitted by the light source on a sample;
measuring a sample spectrum of the sample by detecting light transmitted or reflected by the sample using the detector, the sample spectrum having an intensity value for each of a plurality of wavelengths;
for each of a plurality of reference substances:
retrieving, from a database, a reference spectrum for the respective reference substance, the reference spectrum having intensity values for the plurality of wavelengths;
initially selecting one or more correction values for one or more correction parameters to be applied to at least one of the sample spectrum and the reference spectrum, the one or more correction parameters corresponding to at least one of a clipping correction, a horizontal shift correction, a vertical offset correction, or a baseline correction;
for each of a plurality of iterations:
applying the one or more correction values for the one or more correction parameters to at least one of the sample spectrum and the reference spectrum;
computing a similarity score between the sample spectrum and the reference spectrum resulting from application of the one or more correction values, the similarity score determined using differences between the intensity values of the reference spectrum and corresponding intensity values of the sample spectrum;
determining whether the similarity score satisfies one or more convergence criteria;
upon determining that the similarity score satisfies the one or more convergence criteria, identifying the similarity score as an optimized similarity score corresponding to one or more optimized values of the one or more correction parameters; and upon determining that the similarity score does not satisfy the one or more convergence criteria, updating the one or more correction values for use in performing another iteration until the similarity score satisfies the one or more convergence criteria; and comparing the optimized similarity score to a threshold to determine whether the sample contains the reference substance; and outputting data about one or more of the plurality of reference substances that have optimized similarity scores that are above the threshold.

18. The computer product of claim 17, wherein the one or more correction parameters are a plurality of correction parameters, thereby providing a set of corrections values, and wherein updating the one or more correction values for use in performing the other iteration includes:

for each correction parameter of the plurality of correction parameters:
determining an optimal value for the correction parameter while keeping other correction values fixed, wherein the optimal value is based on optimizing the similarity score; and
updating the plurality of correction values to have the optimal values.

19. The computer product of claim 18, wherein the plurality of corrections parameters includes a first correction parameter, and wherein determining the optimal value for the first correction parameter includes:

for each of a plurality of subiterations:
computing the similarity score between the sample spectrum and the reference spectrum resulting from application of the set of correction values at each of a plurality of correction values of the first correction parameter;
identifying a top similarity score at the sets of correction values;
determining whether the top similarity score satisfies one or more other convergence criteria;
when the top similarity score satisfies the one or more other convergence criteria, identifying the value for the first correction parameter as the optimal value for the first correction parameter; and
when the top similarity score does not satisfy the one or more other convergence criteria, determining new correction values for a next subiteration based on the set of correction values corresponding to the top similarity score.

20. The computer product of claim 17, wherein the one or more correction parameters include a clipping parameter that specifies a maximum intensity value at any wavelength of one of the sample spectrum or the reference spectrum to be used when computing the similarity score.

* * * * *